United States Patent [19]
Bondinell et al.

[11] Patent Number: 4,769,386
[45] Date of Patent: Sep. 6, 1988

[54] IMIDAZOLYLTHIOALKENOIC ACIDS AND -ALKENOLS AND LEUKOTRIENE ANTAGONISTIC COMPOSITION CONTAINING THEM

[75] Inventors: William E. Bondinell, Cherry Hill, N.J.; David T. Hill, North Wales, Pa.; Barry M. Weichman, Skillman, N.J.

[73] Assignee: Smithkline Beckman Corporation, Philadelphia, Pa.

[21] Appl. No.: 923,066

[22] Filed: Oct. 24, 1986

Related U.S. Application Data

[63] Continuation of Ser. No. 740,137, Jun. 3, 1985, abandoned, which is a continuation-in-part of Ser. No. 621,407, Jun. 18, 1984, abandoned.

[51] Int. Cl.$^4$ .................. A61K 31/415; C07D 233/84
[52] U.S. Cl. ..................................... 514/398; 548/337
[58] Field of Search .......................... 548/337; 514/398

[56] References Cited

FOREIGN PATENT DOCUMENTS 68739 1/1983 European Pat. Off. ............ 514/398

Primary Examiner—Mary C. Lee
Assistant Examiner—Kurt G. Briscoe
Attorney, Agent, or Firm—Nancy S. Mayer; Janice E. Williams; Stuart R. Suter

[57] ABSTRACT

The imidazolylthio substituted alkanoic acids represented by the formula (I) or (IA) as defined herein have been found to be leukotriene antagonists and useful in the treatment of diseases in which leukotrienes are a factor, such as asthma.

32 Claims, No Drawings

IMIDAZOLYLTHIOALKENOIC ACIDS AND -ALKENOLS AND LEUKOTRIENE ANTAGONISTIC COMPOSITION CONTAINING THEM

This is a continuation of application Ser. No. 740,137 filed June 3, 1985, now abandoned which is a continuation-in-part of Ser. No. 621,407 filed June 18, 1984, now abandoned.

BACKGROUND OF THE INVENTION

"Slow Reacting Substance of Anaphylaxis" (SRS-A) has been shown to be a highly potent bronchoconstricting substance which is released primarily from mast cells and basophils on antigenic challenge. SRS-A has been proposed as a primary mediator in human asthma. SRS-A, in addition to its pronounced effects on lung tissue, also produces permeability changes in skin and may be involved in acute cutaneous allergic reactions. Further, SRS-A has been shown to effect depression of ventricular contraction and potentiation of the cardiovascular effects of histamine.

The discovery of the naturally occurring leukotrienes and their relationship to SRS-A has reinforced interest in SRS-A and other arachidonate metabolites. SRS-A derived from mouse, rat, guinea pig and man have all been characterized as mixtures of leukotriene-$C_4$ ($LTC_4$), leukotriene-$D_4$ ($LTD_4$) and leukotriene-$E_4$ ($LTE_4$), the structural formulae of which are represented below.

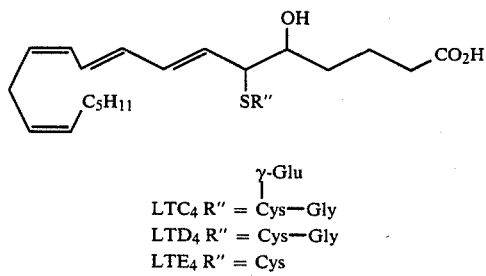

By antagonizing the effects of $LTC_4$, $LTD_4$ and $LTE_4$ or other pharmacologically active mediators at the end organ, e.g. airway smooth muscle, the compounds and pharmaceutical compositions of the instant invention are valuable in the treatment of diseases in which leukotrienes are a factor, such as asthma.

DETAILED DESCRIPTION OF THE INVENTION

The compounds of this invention are represented by the following general structural formulae (I) or (IA):

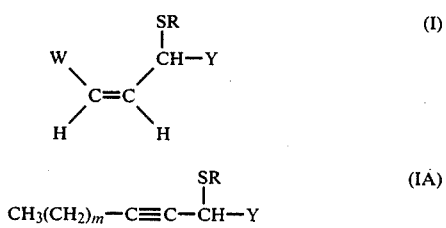

wherein m is 9, 10, 11, 12 or 13; W is $CH_3(CH_2)_m$—,

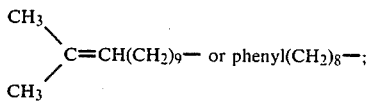

Y is selected from the group consisting of —$CO_2H$, —$CH_2OH$,

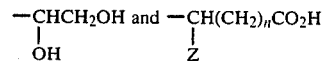

wherein n is 2 or 3 and Z is hydroxyl or hydrogen; and R is selected from the imidazolyl radical of the following formulae (A) or (B)

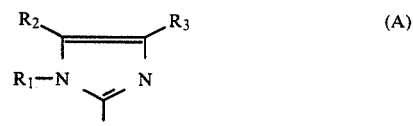

wherein $R_1$ is hydrogen, $C_1$ to $C_4$ alkyl or $C_3$ to $C_4$ alkenyl, $R_2$ is hydrogen, $C_1$ to $C_4$ alkyl, carboxyl or carboxamido, or either —$(CH_2)_pCO_2H$ or —$(CH_2)_pCONH_2$, wherein p is 1 or 2, when $R_1$ and $R_3$ are hydrogen or $C_1$ to $C_4$ alkyl, and $R_3$ is hydrogen, $C_1$ to $C_4$ alkyl or —$CH_2CO_2H$ with the proviso that $R_1$, $R_2$ and $R_3$ cannot all be hydrogen, or

wherein $R_4$ is hydrogen, $C_1$ to $C_4$ alkyl or $C_3$ to $C_4$ alkenyl, $R_5$ is hydrogen, $C_1$ to $C_4$ alkyl or $C_3$ to $C_4$ alkenyl and $R_6$ is hydrogen or carboxyl with the proviso that $R_4$, $R_5$ and $R_6$ cannot all be hydrogen; or a pharmaceutically acceptable salt thereof.

A particular class of the compounds of this invention are those represented by the structural formula (II)

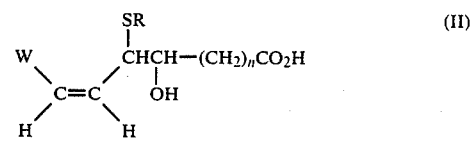

wherein n and R are described above. A subgeneric class of the compounds of formula (II) wherein W is $CH_3(CH_2)_m$— and m is 11; n is 2; and R is the imidazolyl radical of the formula (A) are 6(Z)-nonadecenoic acid derivatives represented by the formula (III)

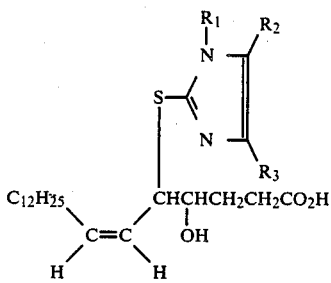

wherein $R_1$, $R_2$ and $R_3$ are described above. The compounds of the formula (III) contain two asymmetric centers, one of which is at carbon atom 4 (i.e. the hydroxyl substituted carbon atom) and one of which is at carbon atom 5 (i.e. the thio substituted carbon atom). This leads to the possibility of four stereoisomers for each compound. In practice, the compounds of this invention of formula (III) have been prepared as a mixture of two stereoisomers, that is the 4R,5S isomer and the 4S,5R isomer. The individual pure stereoisomers are obtainable by preparative high pressure liquid chromatography (HPLC) separation of the appropriate intermediate compounds if those compounds possess a third asymmetric center. A third asymmetric center may be introduced by employing in the synthetic pathway of the desired compounds an asymmetric protecting group, such as an N-trichloroethoxycarbonylprolyl ester. After separation into the individual stereoisomers, the group containing the third asymmetric center is removed by standard procedures.

Representative of these 6(Z)-nonadecenoic acid derivatives are the compounds of the formula (III) wherein $R_1$ is an aklkyl radical containing from one to four carbon atoms or an alkenyl radical containing three to four carbon atoms, and, in particular, wherein $R_1$ is a methyl, ethyl or allyl substitutent. These 5-(1-alkyl-2-imidazolylthio)-6(Z)-nonadecenoic acid and 5-(1-alkenyl-2-imidazolylthio)-6(Z)-nonadecenoic acid derivatives are exemplified by the following compounds:

(A) where $R_2$ is hydrogen
  (1) 4-hydroxy-5-(1-methyl-2-imidazolylthio)-6(Z)-nonadecenoic acid [Formula (III) wherein $R_1$ is methyl and both $R_2$ and $R_3$ are hydrogen];
  (2) 4-hydroxy-5-(1-methyl-4-carboxymethyl-2-imidazolylthio)-6(Z)-nonadecenoic acid [Formula (III) wherein $R_1$ is methyl, $R_2$ is hydrogen and $R_3$ is —$CH_2CO_2H$];
  (3) 4-hydroxy-5-(1-ethyl-2-imidazolylthio)-6(Z)-nonadecenoic acid [Formula (III) wherein $R_1$ is ethyl and both $R_2$ and $R_3$ are hydrogen]; and
  (4) 4-hydroxy-5-(1-allyl-2-imidazolylthio)-6(Z)-nonadecenoic acid [Formula (III) wherein $R_1$ is allyl and both $R_2$ and $R_3$ are hydrogen] and (B) where $R_2$ is a carboxyl radical
  (1) 4-hydroxy-5-(1-methyl-5-carboxy-2-imidazolylthio)-6(Z)-nonadecenoic acid [Formula (III) wherein $R_1$ is methyl, $R_2$ is —$CO_2H$ and $R_3$ is hydrogen] and
  (2) 4-hydroxy-5-(1,4-dimethyl-5-carboxy-2-imidazolylthio)-6(Z)-nonadecenoic acid [Formula (III) wherein both $R_1$ and $R_3$ are methyl and $R_2$ is —$CO_2H$] as the 4R,5S isomer, the 4S,5R isomer or a mixture of the two isomers and (C) where $R_2$ is a carboxamido radical
  (1) 4-hydroxy-5-(1-methyl-5-carboxamido-2-imidazolylthio)-6(Z)-nonadecenoic acid [Formula (III) wherein $R_1$ is methyl, $R_2$ is —$CONH_2$ and $R_3$ is hydrogen] and (D) where $R_2$ is methyl
  (1) 4-hydroxy-5-(1,4,5-trimethyl-2-imidazolylthio)-6(Z)-nonadecenoic acid [Formula (III) wherein $R_1$, $R_2$ and $R_3$ are methyl] and (E) where $R_2$ is carboxymethyl
  (1) 4-hydroxy-5-(1-methyl-5-carboxymethyl-2-imidazolylthio)-6(Z)-nonadecenoic acid [Formula (III) wherein $R_1$ is methyl, $R_2$ is —$CH_2CO_2H$ and $R_3$ is hydrogen].

The 6(Z)-nonadecenoic acid derivatives of the formula (III) are also illustrated by those compounds wherein $R_1$ is hydrogen. Exemplifying these 6(Z)-nonadecenoic acid derivatives are the compounds of the formula (III) wherein $R_2$ is a carboxyl radical, such as, 4-hydroxy-5-[4(5)-carboxy-2-imidazolylthio]-6(Z)-nonadecenoic acid [Formula (III) wherein both $R_1$ and $R_3$ are hydrogen and $R_2$ is —$CO_2H$].

Another subgeneric class of the compounds of formula (II) wherein W is $CH_3(CH_2)_m$— and m is 11; n is 3; and R is the imidazolyl radical of the formula (A) are the 7(Z)-eicosenoic acid derivatives represented by the formula (IV)

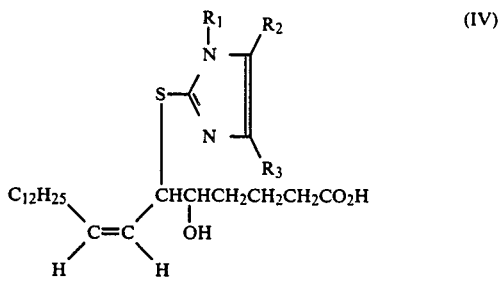

wherein $R_1$, $R_2$ and $R_3$ are described above.

Representative of these 7(Z)-eicosenoic acid derivatives are the compounds of the formula (IV) wherein $R_1$ is an alkyl radical containing from one to four carbon atoms and, in particular, wherein $R_1$ is a methyl substituent. These 6-(1-alkyl-2-imidazolylthio)-7(Z)-eicosenoic acid derivatives are exemplified by 5-hydroxy-6-(1-methyl-2-imidazolylthio)-7(Z)-eicosenoic acid [Formula (IV) wherein $R_1$ is methyl and both $R_2$ and $R_3$ are hydrogen]. Since the 7(Z)-eicosenoic acid derivatives of the formula (III) also contain two asymmetric centers at carbon atom 5 and carbon atom 6, these compounds have been prepared in a mixture of two stereoisomers, that is the 5R,6S isomer and the 5S,6R isomer.

A second particular class of the compounds of this invention are those represented by the structural formula (II) wherein R is the imidazolyl radical of formula (B). Specifically, this class of compounds is illustrated by the compounds of the formula (II) wherein W is $CH_3(CH_2)_m$— and m is 11; and n is 2, which are also 6(Z)-nonadecenoic acid derivatives represented by the formula (V)

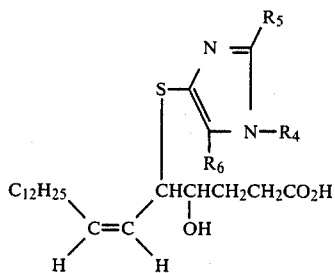

(V)

wherein $R_4$, $R_5$ and $R_6$ are described above.

Representative of these 6(Z)-nonadecenoic acid derivatives are the compounds of the formula (V) wherein $R_4$ is an alkyl radical containing from one to four carbon atoms, and, in particular, wherein $R_4$ is a methyl substituent. These 5-(1-alkyl-4-imidazolylthio)-6(Z)-nonadecenoic acid derivatives are exmplified by 4-hydroxy-5-(1-methyl-5-carboxy-4-imidazolylthio)-6(Z)-nonadecenoic acid [Formula (V) wherein $R_4$ is methyl, $R_5$ is hydrogen and $R_6$ is —$CO_2H$] and 4-hydroxy-5-(1-methyl-4-imidazolylthio)-6(Z)-nonadecenoic acid, sodium salt [Formula (V) wherein $R_4$ is methyl and $R_5$ and $R_6$ are both hydrogen].

Another particular class of the compounds of this invention are those compounds represented by the structural formula (VI)

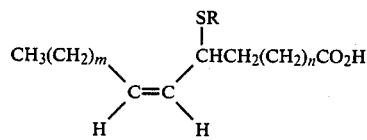

(VI)

wherein m, n and R are described above. Specifically, this class of compounds is illustrated by those compounds wherein m is 11, n is 2 and R is the imidazolyl radical of the formula (A), which are 6(Z)-nonadecenoic acid derivatives. These 6(Z)-nonadecenoic acid derivatives are exemplified by 5-(1-methyl-5-carboxy-2-imidazolylthio)-6(Z)-nonadecenoic acid.

A further class of the compounds of this invention are those compounds represented by the structural formula (VII)

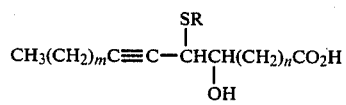

(VII)

wherein m, n and R are described above. Specifically, this class of compounds is illustrated by those compounds wherein m is 11, n is 2 and R is the imidazolyl radical of the formula (A), which are 6-nonadecynoic acid derivatives. Representative of the 6-nonadecynoic acid derivatives is 4-hydroxy-5-(1,4-dimethyl-5-carboxy-2-imidazolylthio)-6-nonadecynoic acid.

Additionally, another class of the compounds of this invention are those compounds represented by the structural formula (VIII)

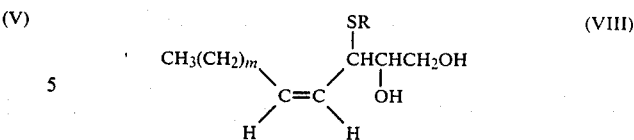

(VIII)

wherein m and R are described above. Specifically, this class of compounds is illustrated by those compounds wherein m is 11 and R is an imidazolyl radical of the formula (A), which are 1,2-dihydroxy-4(Z)-heptadecene derivatives. These 1,2-dihydroxy-4(Z)-heptadecene derivatives are exemplified by 2-hydroxy-3-(1-methyl-5-carboxy-2-imidazolylthio)-4(Z)-heptadecen-1-ol.

Another class of the compounds of this invention are those compounds represented by the structural formula (IX)

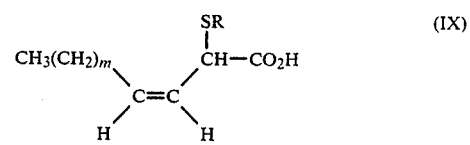

(IX)

wherein m and R are described above. Specifically, this class of compounds is illustrated by those compounds wherein m is 11 and R is an imidazolyl radical of the formula (A), which are 3(Z)-hexadecenoic acid derivatives. These 3(Z)-hexadecenoic acid derivatives are exemplified by 2-(1-methyl-5-carboxy-2-imidazolylthio)-3(Z)-hexadecenoic acid.

A further class of the compounds of this invention are those compounds represented by the structural formula (X)

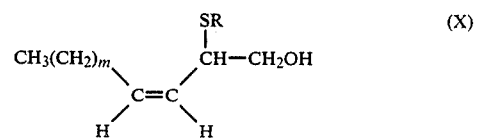

(X)

wherein m and R are described above. Specifically, the class of compounds is illustrated by those compounds where m is 11 and R is an imidazolyl radical of the formula (A), which are 3(Z)-hexadecen-1-ol derivatives. These 3(Z)-hexadecen-1-ol derivatives are exemplified by 2-(1-methyl-5-carboxy-2-imidazolylthio)-3(Z)-hexadecen-1-ol.

The compounds of the present invention are amphoteric and are, therefore, capable of forming salts with pharmaceutically acceptable acids and bases, according to procedures well known in the art. Such acceptable acids include mineral and organic acids, such as hydrochloric, sulfuric, methanesulfonic, benzene sulfonic, p-toluenesulfonic, and acetic acid. Such acceptable bases include organic and inorganic bases, such as ammonia, organic amines, and alkali metal bases.

The compounds of the formula (II) are readily prepared by reacting the appropriate 2-thioimidazole of the formula (C) or the 4-thioimidazole of the formula (D)

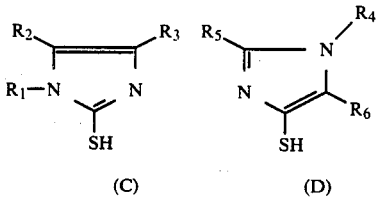

wherein $R_1$, $R_2$, $R_3$, $R_4$, $R_5$ and $R_6$ are described above, with the appropriate epoxyalkenoic acid derivative of the formula (E)

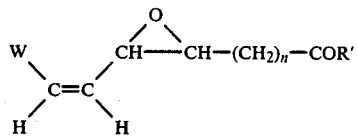

wherein n is described above and R' is a radical easily convertible to —OH, such as an alkoxy radical containing from one to six carbon atoms. The amount of the thioimidazole reactant can be between 0.5 and 2.0 moles per mole of the compound of the formula (E). The reaction of either thioimidazole of the formula (C) or (D), preferably in excess amount, with the epoxyalkenoic acid derivative of the formula (E) occurs under mild conditions in the presence of a non-nucleophilic base and an inert solvent. Examples of the non-nucleophilic bases which are employed in this reaction include tertiary alkylamines, such as triethylamine, tertiary alkylarylamines, such as N,N-dimethylaniline, aromatic amines, such as pyridine, inorganic alkali carbonates, such as potassium carbonate, and inorganic alkali bicarbonates, such as sodium bicarbonate. Examples of inert solvents utilized in this reaction include alcohols such as methanol, ethanol and isopropanol, halogenated solvents, such as dichloromethane and chloroform, and amides, such as dimethylformamide and dimethylacetamide. The temperature range of this reaction is from 0° to 100° C. but an ambient temperature is preferred.

The compounds of the formulae (C) and (D) are known compounds or are conveniently prepared employing standard chemical reactions. Preferably these reactants bearing a carboxyl, carboxymethyl or carboxyethyl substituent as set forth in formulae (A) and (B) above are employed as the corresponding carboalkoxy derivatives wherein the alkoxy radical contains from one to six carbon atoms. When present, the alkoxy substituent is subsequently hydrolyzed to give the free carboxyl, carboxymethyl or carboxyethyl substituted products of formula (I).

The compounds of the formula (E) are prepared by reacting either 4,5-epoxy-6-oxo-hexanoate ester or 5,6-epoxy-7-oxoheptanoate ester with an appropriate alkyltriphenyl phosphonium ylid according to the general procedure disclosed and claimed in U.S. Pat. No. 4,352,757.

The compounds of the formula (VI) are readily prepared via the following synthetic pathway:

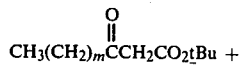

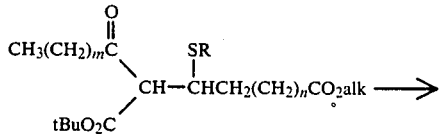

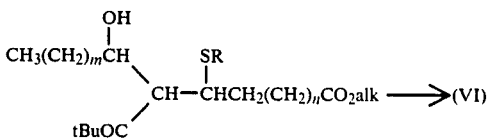

The appropriate t-butyl 3-oxo-alkanoate (1) is reacted under basic conditions with either 5-oxovalerate alkyl ester or 6-oxohexanoate alkyl ester [Compound (2) wherein alk is an alkyl radical of one to six carbon atoms and n is 2 and 3 respectively] and the appropriate thiol, with any labile substituents in protected form, is then added to yield the compounds of the formula (3). The compounds of the formula (3) are then reduced to the compounds of formula (4), the t-butyl protecting group removed under acidic conditions. The resulting β-hydroxy acids are treated with the dineopentyl acetal of dimethyl formamide to give after the deprotection of any labile groups the compounds of formula (VI).

The compounds of the formula (VII) are readily prepared via the following synthetic pathway:

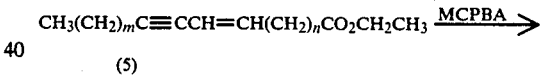

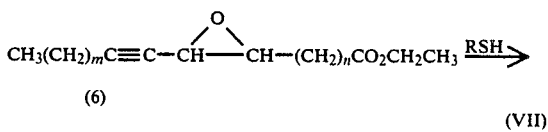

The compounds of the formula (5) wherein n is 2 are obtained by reaction of the appropriate alkyne, $CH_3(CH_2)_mC{\equiv}CH$, with ethyl grignard and then acrolein to give the compounds of formula (7),

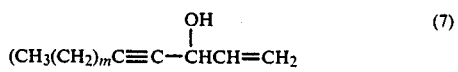

The latter then are reacted with triethyl orthoacetate to afford compounds of formula (5), n is 2. To obtain the compounds of the formula (5) wherein n is 3, an appropriate bromo alkyne, $CH_3(CH_2)_mC{\equiv}CCH_2Br$, and triphenylphosphine are reacted to give the corresponding triphenylphosphonium bromide. Treatment of this salt with sodium ethoxide followed by reaction with ethyl 5-oxopentanoate yields compounds of formula (5), n is 3, after chromatographic separation of the cis and trans isomers.

The compounds of the formula (5) are epoxidized using metachloroperbenzoic acid (MCPBA) to yield the compounds of the formula (6) which are converted into the compounds of formula (VII) utilizing the procedures outlined above.

The compounds of the formula (VIII) are readily prepared via the following synthetic pathway:

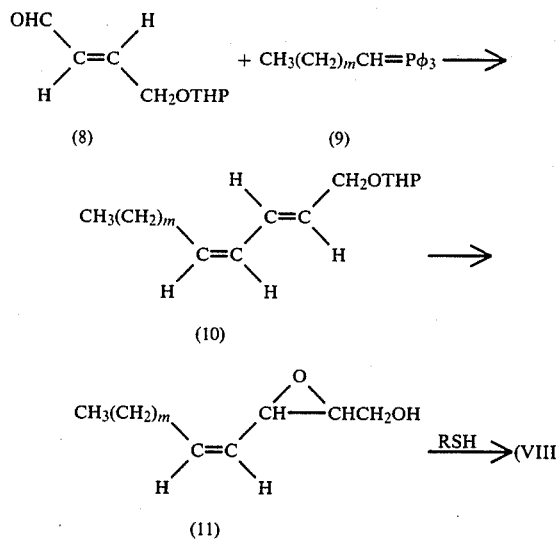

Compound (8) wherein THP is a tetrahydropyranyl radical is reacted with the appropriate alkyltriphenyl phosphonium ylid (9) under Wittig conditions to give compounds of the formula (10). The compounds of the formula (10) are hydrolyzed to cleave the THP ether and then epoxidized to afford compounds of the formula (11), which are converted into compounds of the formula (VIII) utilizing procedures outlined above.

The compounds of the formulae (IX) and (X) are prepared by employing the following intermediates:

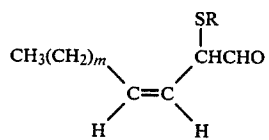

which are obtained from the compounds of the formula (VIII) by oxidative cleavage. Compound (12) may either be oxidized to give compounds of formula (IX) or reduced to give compounds of formula (X).

The leukotriene antagonist activity of the compounds of this invention is measured by the ability of the compounds to inhibit the leukotriene induced contraction of guinea pig tracheal tissues in vitro. The following methodology was employed:

In vitro: Guinea pig (adult male albino Hartley strain) tracheal spiral strips of approximate dimensions 2 to 3 mm cross-sectional width and 3.5 cm length were bathed in modified Krebs buffer in jacketed 10 ml tissue bath and continuously aerated with 95% $O_2$/5% $CO_2$. The tissues were connected via silk suture to force displacement transducers for recording isometric tension. The tissues were equilibrated for 1 hr., pretreated for 15 minutes with meclofenamic acid (1 $\mu$M) to remove intrinsic prostaglandin responses, and then pretreated for an additional 30 minutes with either the test compound or vehicle control. A cumulative concentration-response curve for $LTD_4$ on triplicate tissues was generated by successive increases in the bath concentration of the $LTD_4$. In order to minimize intertissue variability, the contractions elicited by $LTD_4$ were standardized as a percentage of the maximum response obtained to a reference agonist, carbachol (10M).

Calculations: The averages of the triplicate $LTD_4$ concentration-response curves both in the presence and absence of the test compound were plotted on log graph paper. The concentration of $LTD_4$ needed to elicit 30% of the contraction elicited by carbachol was measured and defined as the $EC_{30}$. The $-\log K_B$ value for the test compound was determined by the following equations:

1. $\dfrac{EC_{30} \text{ (presence of test compound)}}{EC_{30} \text{ (presence of vehicle control)}} = \text{dose ratio} = X$ 2. $K_B$ = concentration of test compound/(X-1)

| Compounds of the Formula (III) | | | |
|---|---|---|---|
| $R_1$ | $R_2$ | $R_3$ | In Vitro $-\log K_B$ |
| $CH_3$ | H | H | 5.9 |
| $CH_3$ | H | $-CH_2CO_2H$ | 6.1 |
| $CH_3CH_2$ | H | H | 5.3 |
| $CH_2=CHCH_2$ | H | H | 5.3 |
| $CH_3$ | $-CO_2H$ | H | 6.8 |
| $CH_3$ | $-CO_2H$ | $CH_3$ | 6.9 |
| [a]$CH_3$ | $-CO_2H$ | $CH_3$ | 6.9 |
| [a]$CH_3$ | $-CO_2H$ | $CH_3$ | 6.8 |
| $CH_3$ | $-CONH_2$ | H | 5.4 |
| $CH_3$ | $CH_3$ | $CH_3$ | 5.6 |
| H | $-CO_2H$ | H | 5.7 |
| $CH_3$ | $-CH_2CO_2H$ | $CH_3$ | 6.4 |
| $CH_3$ | $-CO_2H$ | $-CH_2CH_3$ | 6.7 |
| $CH_3$ | $-CO_2H$ | $-CH_2CH_2CH_3$ | 6.5 |
| $CH_3$ | $-CO_2H$ | $-CH(CH_3)_2$ | 5.9 |
| $CH_3$ | $-CH_2CH_2CO_2H$ | $CH_3$ | 5.9 |
| $CH_3$ | $-CH_2CONH_2$ | $CH_3$ | 6.2 |

| Compounds of the Formula (IV) | | | |
|---|---|---|---|
| $R_1$ | $R_2$ | $R_3$ | In Vitro $-\log K_B$ |
| $CH_3$ | H | H | 6.0 |

| Compounds of the Formula (V) | | | |
|---|---|---|---|
| $R_4$ | $R_5$ | $R_6$ | In Vitro $-\log K_B$ |
| [b]$CH_3$ | H | H | 5.7 |
| $CH_3$ | H | $-CO_2H$ | 6.7 |

| Compounds of the Formula (VI) | | | | |
|---|---|---|---|---|
| m | n | R | | In Vitro $-\log K_B$ |
| 11 | 2 | A | where $R_1$ is $CH_3$, $R_2$ is $-CO_2H$, $R_3$ is H | 6.5 |

| Compounds of the Formula (VII) | | | | |
|---|---|---|---|---|
| m | n | R | | In Vitro $-\log K_B$ |
| 11 | 2 | A | where $R_1$ is $CH_3$, $R_2$ is $-CO_2H$, $R_3$ is $CH_3$ | 5.8 |

| Compounds of the Formula (VIII) | | | |
|---|---|---|---|
| m | R | | In Vitro $-\log K_B$ |
| 11 | A | where $R_1$ is $CH_3$, $R_2$ is $-CO_2H$, $R_3$ is H | 5.6 |

[a] 4S,5R isomer or 4R,5S isomer
[b] Sodium Salt

The specificity of the antagonist activity of a number of the compounds of this invention is demonstrated by relatively low levels of antagonism toward agonists such as potassium chloride, carbachol, histamine and PGF$_2\alpha$.

Pharmaceutical compositions of the present invention comprise a pharmaceutical carrier or diluent and an amount of a compound of the formulae (I) or (IA), or a pharmaceutically acceptable salt, such as an alkali metal salt thereof, sufficient to antagonize the effects of leukotrienes, such as the symptoms of asthma and other hypersensitivity diseases.

When the pharmaceutical composition is employed in the form of a solution or suspension, examples of appropriate pharmaceutical carriers or diluents include: for aqueous systems, water; for non-aqueous systems, ethanol, glycerin, propylene glycol, corn oil, cottonseed oil, peanut oil, sesame oil, liquid parafins and mixtures thereof with water; for solid systems, lactose, kaolin and mannitol; and for aerosol systems, dichlorodifluoromethane, chlorotrifluoroethane and compressed carbon dioxide. Also, in addition to the pharmaceutical carrier or diluent, the instant compositions may include other ingredients such as stabilizers, antioxidants, preservatives, lubricants, suspending agents, viscosity modifiers and the like, provided that the additional ingredients do not have a detrimental effect on the therapeutic action of the instant compositions.

The nature of the composition and the pharmaceutical carrier or diluent will, of course, depend upon the intended route of administration, i.e. parenterally or by inhalation.

In general, particularly for the prophylactic treatment of asthma, the compositions will be in a form suitable for administration by inhalation. Thus the compositions will comprise a suspension or solution of the active ingredient in water for administration by means of a conventional nebulizer. Alternatively the compositions will comprise a suspension or solution of the active ingredient in a conventional liquified propellant or compressed gas to be administered from a pressurized aerosol container. The compositions may also comprise the solid active ingredient diluted with a solid diluent for administration from a powder inhalation device. In the above compositions, the amount of carrier or diluent will vary but preferably will be the major proportion of a suspension or solution of the active ingredient. When the diluent is a solid it may be present in less, equal or greater amounts than the solid active ingredient.

For parenteral administration the pharmaceutical composition will be in the form of a sterile injectable liquid such as an ampul or an aqueous or nonaqueous liquid suspension.

For topical administration the pharmaceutical composition will be in the form of a cream of ointment.

Usually a compound of the formulae (I) or (IA) is administered to an animal subject in a composition comprising a nontoxic amount sufficient to antagonize the leukotriene effects, such as to produce an inhibition of the symptoms of an allergic response. When employed in this manner, the dosage of the composition is selected from the range of from 350 mg. to 700 mg. of active ingredient for each administration. For convenience, equal doses will be administered 1 to 4 times daily with the daily dosage regimen being selected from about 350 mg. to about 2800 mg.

The pharmaceutical preparations thus described are made following the conventional techniques of the pharmaceutical chemist as appropriate to the desired end product.

Included within the scope of this disclosure is a method of antagonizing leukotriene effects, such as the method of inhibiting the symptoms of an allergic response resulting from a mediator release, which comprises administering to an animal subject a nontoxic effective amount for producing said antagonism of a compound of the formulae (I) or (IA), preferably in the form of a pharmaceutical composition. The administration may be carried out in dosage units are suitable intervals or in single doses as needed. Usually this method will be practiced when relief of allergic symptoms is specifically required. However, the method is also usefully carried out as continuous or prophylactic treatment. It is within the skill of the art to determine by routine experimentation the effective dosage to be administered from the dose range set forth above, taking into consideration such factors as the degree of severity of the allergic condition being treated, and so forth.

The following examples illustrate the preparation of the compounds of this invention and their incorporation into pharmaceutical compositions and as such are not to be considered as limiting the invention set forth in the claims appended hereto.

EXAMPLE 1

Preparation of 4-Hydroxy-5-(1-methyl-4-carboxymethyl-2-imidazolylthio)-6(Z)-nonadecenoic acid (a) To a solution of methyl 4,5-epoxy-6(Z)-nonadecenoate (1.95 mmoles) in absolute methanol (10 ml) at 0° to 5° C. was added under argon the ethyl ester of 4-carboxymethyl-1-methyl-2-thioimidazole (prepared as described below) (3.31 mmoles) in absolute methanol (10 ml) and triethylamine (4.89 mmoles). The resultant mixture was stirred overnight at ambient temperature and then evaporated to dryness at reduced pressure to give a crude mixture of products. This mixture was triturated with a mixture of hexane (15 ml) and ethyl acetate (10 ml) and filtered. The filtrate was flash chromatographed on silica gel eluted with a mixture of hexane (300 ml):ethyl acetate (250 ml) to yield a mixture of methyl 4-hydroxy-5-(1-methyl-4-methoxycarbonylmethyl-2-imidazolylthio)-6(Z)-nonadecenoate and methyl 4-hydroxy-5-(1-methyl-4-ethoxycarbonylmethyl-2-imidazolylthio)-6(Z)-nonadecenoate.

(b) To the mixture of methyl 4-hydroxy-5-(1-methyl-4-methoxycarbonylmethyl-2-imidazolylthio)-6(Z)-nonadecenoate and methyl 4-hydroxy-5-(1-methyl-4-ethoxycarbonylmethyl-2-imidazolylthio)-6(Z)-nonadecenoate (1.52 mmoles) in methanol (17 ml) at 5° C. was added 10% aqueous sodium hydroxide (3.84 ml) dropwise over 3 minutes with stirring. The reaction mixture was stirred at ambient temperature overnight. The reaction mixture was then acidified with 3N hydrochloric acid and evaporated to an oil. The oil was diluted with water (15 ml), cooled and extracted with ethyl acetate (2×20 ml). The organic phase was treated with brine (20 ml), dried over magnesium sulfate, filtered and evaporated to yield an oil. The oil was triturated with diethyl ether:petroleum ether (1:1) to give the desired product as an amorphous solid with a melting point of 50°–60° C.

Elemental Analysis for $C_{25}H_{42}N_2O_5S$: Calculated: C, 62.21; H, 8.77; N, 5.80; S, 6.64. Found: C, 61.99; H, 8.64; N, 5.66; S, 6.73.

(c) 4-Carboxymethyl-1-methyl-2-thioimidazole ethyl ester was prepared in two steps as follows:

(1) To a solution of N-benzylmethylamine (22 mmoles) in ethyl acetate (125 ml) at 0° C. was added ethyl 4-chloroacetoacetate (10 mmoles) in ethyl acetate (30 ml). The reaction mixture was stirred for 3 hours at 10°-15° C. and then filtered. The filtrate was chromatographed on silica (150 g) eluted with hexane:ethyl acetate (4:1) to give the desired intermediate, ethyl 4-(N-benzyl-N-methylamino)-acetoacetate.

(2) To a solution of this intermediate (3.3 mmoles) in ethanol (40 ml) was added 10% Pd/C in ethanol (10 ml) and hydrogen chloride in ethanol (9.9 mmoles in 70 ml). The solution was hydrogenated at 40 psi for three hours to remove the benzyl group. Potassium thiocyanate (3.8 mmoles) in water (50 ml) was added to the reaction mixture and the Pd/C catalyst filtered off. The filtrate was heated at 50°-60° C. for 2 hours and evaporated to dryness to yield the crude product as an oil. The oil was dissolved in ethyl acetate and chromatographed on silica (120 g) eluted with ethyl acetate to afford the desired product (mp 95°-96.5° C.).

EXAMPLE 2

Preparation of 4-Hydroxy-5-(1-methyl-5-carboxy-2-imidazolylthio)-6(Z)-nonadecenoic acid Employing the general procedure of Example 1(a) and 1(b) methyl 4,5-epoxy-6(Z)-nonadecenoate (3.79 mmoles) was reacted with 1-methyl-5-carbomethoxy-2-thioimidazole (6.82 mmoles) to afford the desired compound as a solid with a melting point of 126°-127° C.

Analysis for $C_{24}H_{40}N_2O_5S$: Calculated: C, 61.51; H, 8.60; N, 5.98; S, 6.84. Found: C, 61.43; H, 8.69; N, 5.98; S 6.68.

EXAMPLE 3

Preparation of 4-Hydroxy-5-(1,4-dimethyl-5-carboxy-2-imidazolylthio)-6(Z)-nonadecenoic acid (a) Employing the general procedure of Example 1(a) and 1(b) methyl 4,5-epoxy-6(Z)-nonadecenoate (1.89 mmoles) was reacted with 1,4-dimethyl-5-carboethoxy-2-thioimidazole (3.22 mmoles) to afford the desired compound as a solid (mp 130°-131.5° C.).

Analysis for $C_{25}H_{42}N_2O_5S$: Calculated: C, 62.21; H, 8.77; N, 5.80; S, 6.64. Found: C, 61.82; H, 8.58; N, 5.81; S, 6.77.

(b) Separation of isomers

To a solution of methyl 4-hydroxy-5-(1,4-dimethyl-5-carbomethoxy-2-imidazolylthio)-6(Z)-nonadecenoate (0.75 mmoles) in sieve-dried pyridine (8 ml) was added under argon at 0° C. freshly prepared N-trichloroethoxycarbonylprolyl chloride (7.45 mmoles) in sieve-dried pyridine (12 ml). The reaction mixture was allowed to warm to ambient temperature and stirred for about a day. The reaction mixture was poured onto ice-water (50 ml) and then extracted with ethyl acetate (2×25 ml). The organic phase was washed four times with a mixture of brine (10 ml) and 5% aqueous sodium bicarbonate (10 ml), filtered, dried over anhydrous magnesium sulfate and concentrated in vacuo. The resultant oil was flash chromatographed on silica gel eluted with 75:25 hexane:ethyl acetate to yield a mixture of the two desired compounds. These compounds were separated by chromatography on a magnum silica column eluted with hexane-ethyl acetate (3:1).

(c) Each of the resultant individual compounds was separately dissolved in methanol (~10 ml) at 0°-5° C. To the stirred solution was added 10% aqueous sodium hydroxide (10 equiv.) and the reaction mixture was allowed to warm to ambient temperature overnight. The reaction mixture was concentrated in vacuo, diluted with water (~10 ml), cooled to 0°-5° C. and acidified with 3N hydrochloric acid to a pH 4 to precipitate out the desired compound. Diethyl ether (5 ml) was added to the precipitate and the solids filtered and air dried. The resultant solid was triturated in diethyl ether to afford the desired individual compounds as pure isomers.

Isomer A (mp 118°-119° C.) and Isomer B (mp 118.5°-119.5° C.)

EXAMPLE 4

Preparation of 4-Hydroxy-5-[4(5)-carboxy-2-imidazolylthio]-6(Z)-nonadecenoate acid Employing the general procedure of Example 1(a) and 1(b), methyl 4,5-epoxy-6(Z)-nonadecenoate (1.84 mmoles) was reacted with 4(5)-carbomethoxy-2-thioimidazole (3.31 mmoles) to afford the desired product as solid (mp 88°-89.5° C.).

Analysis for $C_{23}H_{38}N_2O_5S$: Calculated: C, 57.36; H, 8.58; N, 5.82; S, 6.66. Found: C, 57.22; H, 8.34; N, 5.84; S, 6.71.

EXAMPLE 5

Preparation of 4-Hydroxy-5-(1-methyl-5-carboxy-4-imidazolylthio)-6(Z)-nonadecenoic acid Employing the general procedure of Example 1(a) and 1(b) methyl 4,5-epoxy-6(Z)-nonadecenoate (1.93 mmoles) was reacted with 1-methyl-5-carboethoxy-4-thioimidazole (3.4 mmoles) to afford the desired product as a solid (mp 96°-98° C.).

Analysis for $C_{24}H_{40}N_2O_5S$: Calculated: C, 61.51; H, 8.60; N, 5.98. Found: C, 61.85; H, 8.67; N, 6.14.

EXAMPLES 6-12

The following compounds were prepared by utilizing the general procedure of Example 1(a) and 1(b) from the appropriate starting materials.

4-Hydroxy-5-(1-methyl-2-imidazolylthio)-6(Z)-nonadecenoic acid (mp 82°-83.5° C.);

4-Hydroxy-5-(1-methyl-5-carboxamido-2-imidazolylthio)-6(Z)-nonadecenoic acid (mp 107.5°-109° C.);

5-Hydroxy-6-(1-methyl-2-imidazolylthio)-7(Z)-eicosenoic acid (mp 58°-60.5° C.);

4-Hydroxy-5-(1-ethyl-2-imidazolylthio)-6(Z)-nonadecenoic acid, sodium salt (mp 67.5°-69° C.);

4-Hydroxy-5-(1-allyl-2-imidazolylthio)-6(Z)-nonadecenoic acid (mp 81°-83° C.);

4-Hydroxy-5-(1,4,5-trimethyl-2-imidazolylthio)-6(Z)-nonadecenoic acid (mp 42°-44° C.); and 4-Hydroxy-5-(1-methyl-4-imidazolylthio)-6(Z)-nonadecenoic acid, sodium salt (mp 67.5°-69° C.).

EXAMPLE 13

Preparation of
5-(1-methyl-5-carboxy-2-imidazolylthio)-6(Z)-nonadecenoic acid (a) Methyl 5-(1-methyl-5-carbomethoxy-2-imidazolylthio)-6-t-butoxycarbonyl-7-oxo-nonadecenoic acid To a solution of t-butyl 3-oxo-pentadecanoate (2.9 mmoles) and methyl 5-oxo-pentanoate (2.9 mmoles) in methylene chloride (20 ml) was added at ambient temperature, with stirring, piperidine (4.4 mmoles) and the reaction mixture stirred for 2 hours. 1-Methyl-5-carbomethoxy-2-thioimidazole (2.9 mmoles) was then added to the reaction mixture which was stirred overnight at ambient temperature. The desired compound was isolated from the reaction mixture by flash chromatography on silica gel eluted with 80:20 hexane:ethyl acetate.

(b) Methyl 5-(1-methyl-5-carbomethoxy-2-imidazolylthio)-6-t-butoxycarbonyl-7-hydroxy-nonadecanoic acid To a solution of a compound prepared according to Example 13(a) (18.0 mmoles) in absolute ethanol (39 ml) and ethyl acetate (19 ml) at −10° C. was added sodium borohydride (18.0 mmoles) in ethyl acetate (20 ml). The reaction mixture was stirred for approximately 1½ hours at between −10° and 0° C. The reaction mixture was treated with brine (50 ml), water (50 ml) and then 5% aqueous sodium bicarbonate (50 ml). The organic phase was separated, dried over anhydrous magnesium sulfate, filtered and concentrated in vacuo to yield crude material. This material was purified by flash chromatography on silica gel eluted with 70:30 hexane:ethyl acetate to give the desired compound.

(c) Methyl 5-(1-methyl-5-carbomethoxy-2-imidazolylthio)-6(Z)-nonadecenoic acid

To a solution of the compound of Example 13(b) (9.5 mmoles) in chloroform (51 ml) at 0° C. under argon was added trifluoroacetic acid (0.52 moles) and the reaction mixture allowed to warm to ambient temperature for about 5 hours. Chloroform (30 ml) was added to the reaction mixture and then the dineopentylacetal of dimethylformamide (57.2 mmoles) was added with the temperature maintained below 30° C. Additional chloroform (14 ml) was added and reaction mixture refluxed for about 3 hours and then cooled. The reaction mixture was flash chromatographed on silica gel eluted with 70:30 hexane:ethyl acetate to give the desired compound.

(d) To a solution of the compound of Example 13(c) (1.0 mmole) in methanol (12 ml) under argon at 5° C. was added 10% aqueous sodium hydroxide (2.4 ml) and the reaction mixture warmed to ambient temperature. The reaction mixture was then cooled and acidified to a pH of 1.0 with 3N hydrochloric acid. The desired product was extracted from the reaction mixture with ethyl acetate. The ethyl acetate solution was dried over anhydrous magnesium sulfate, filtered and concentrated in vacuo to yield 5-(1-methyl-5-carboxy-2-imidazolylthio)-6(Z)-nonadecenoic acid (mp 96°–99° C.).

Analysis for $C_{24}H_{40}N_2O_4S$: Calculated: C, 63.68; H, 8.91; N, 6.19. Found: C, 63.47; H, 8.77; N, 6.15.

EXAMPLE 14

Preparation of
4-Hydroxy-5-(1,4-dimethyl-5-carboxy-2-imidazolylthio)-6-nonadecynoic acid (a) 1-Heptadecen-4-yn-3-ol To freshly prepared ethyl magnesium bromide (from 58.95 mmoles of bromoethane and 49.36 mmoles of magnesium) in diethyl ether (125 ml) was added 1-tetradecyne (44.5 mmoles) in diethyl ether (25 ml) dropwise at ambient temperature. After 3 hours the reaction mixture was cooled to −10° C. and freshly distilled acrolein (59.86 mmoles) in diethyl ether (25 ml) was added dropwise. After 30 minutes saturated ammonium chloride (100 ml) and water (50 ml) were added. The organic phase was separated, washed with brine (100 ml) and dried over anhydrous magnesium sulfate. The desired compound was purified by flash chromatography on silica gel eluted with 90:10 hexane:ethyl acetate.

(b) Ethyl 4-nonadecen-6-ynoate

A solution of the compound of Example 14(a) (8.07 mmoles) and propionic acid (4 drops) in triethyl orthoacetate (54.55 mmoles) was heated for 1 hour at 140° C. and the ethanol produced in the reaction distilled off. The reaction mixture was cooled and concentrated in vacuo. The resultant yellow oil was purified by flash chromatography on silica gel eluted with 90:10 petroleum ether:ethyl acetate to yield the desired compound.

(c) To a solution of the compound of Example 14(b) (2.84 mmoles) in methylene chloride (25 ml) under argon at 0° C. was added meta-chloroperbenzoic acid (2.86 mmoles) in methylene chloride (10 ml) and the reaction mixture stirred for about 20 hours at ambient temperature. Diethyl ether (50 ml) was added to the reaction mixture which was then washed with 5% aqueous sodium bicarbonate (50 ml) and saturated sodium chloride (50 ml). The organic phase was dried over anhydrous magnesium sulfate, filtered and concentrated in vacuo. The resultant material was purified by flash chromatography on silica gel eluting with 92:8 petroleum ether:ethyl acetate to afford ethyl 4,5-epoxy-6-nonadecynoate which was converted by reaction with 1,4-dimethyl-5-carboethoxy-2-thioimidazole into the desired product utilizing the general procedure of Example 1(a) and 1(b) (mp 136°–138° C.).

Analysis for $C_{25}H_{40}N_2O_5S$: Calculated: C, 62.47; H, 8.39; N, 5.83. Found: C, 62.45; H, 8.32; N, 5.87.

EXAMPLE 15

Preparation of
5-Hydroxy-6-(1,4-dimethyl-5-carboxy-2-imidazolylthio)-7-eicosynoic acid 1-Bromo-2-pentadecyne (0.01 mole) and triphenylphosphine (0.01 mole) are mixed in ether to give pentadec-2-ynyl-triphenylphosphonium bromide. The salt (0.01 mole) is dissolved in absolute ethanol containing one equivalent of sodium ethoxide. Ethyl 5-oxopentanoate (0.01 mole) is added and the mixture is refluxed for 24 hours to give a mixture of cis-and-trans ethyl 5-eicosen-7-ynoate. The isomers are separated by chromatography and the trans isomer is converted to 5-hydroxy-6-(1,4-dimethyl-5-carboxy-2-imidazolylthio)-7-eicosynoic acid as described in Example 14(c).

EXAMPLE 16

Preparation of 2-Hydroxy-3-(1-methyl-5-carboxy-2-imidazolylthio)-4(Z)-heptadecen-1-ol (a) Heptadec-2,4-dien-1-ol tetrahydropyranyl ether Tridecyltriphenyl phosphonium bromide (0.3 mole) was dissolved in 900 ml of tetrahydrofuran and cooled to 0° C. in an ice-salt bath while stirring under argon. A 2.2N solution of n-butyllithium in hexane (0.36 mole) was added dropwise over a period of 30 minutes. The mixture was stirred for an additional 20 minutes and then cooled to −70° C. in a dry ice-acetone bath. The 4-hydroxybut-2(E)-ene-1-al tetrahydropyranyl ether (0.3 mole) in 225 ml of tetrahydrofuran was added dropwise over a period of 35 minutes and the mixture stirred for an additional hour at −70° C. The mixture was then poured into 6.25 liters of ether and stirred for 20 minutes. The resulting mixture was filtered through glass fiber filter paper. The filtrate was evaporated and the residue triturated with hexane, filtered and evaporated to give a ~3:1 mixture of trans:cis isomers of the desired compound.

(b) Heptadec-2,4-dien-1-ol

The mixture of compounds from Example 16(a) (0.24 mole) was dissolved in 3 liters of methanol and pyridine p-toluenesulfonic acid (0.012 mole) was added to the mixture, with stirring under argon at room temperature. The progress of the reaction was monitored by thin layer chromatography. When the reaction was complete the solvent was evaporated and the residue flash chromatographed on silica gel eluted with 90:10 hexane:ethyl acetate to give a 3:1 mixture of the resulting trans:cis isomers. Separation was accomplished by careful chromatography on silica gel.

(c) Trans 2,3-epoxy-4(Z)-heptadecen-1-ol

The trans isomer of Example 14(b) (10 mmol) was dissolved in 100 ml of methylene chloride, stirring at room temperature under argon. A 0.5N solution of sodium bicarbonate (30 ml) was added. The 85% m-chloroperbenzoic acid (10 mmol) was added slowly in small portions. The mixture was stirred for 1.5 hours after the addition was complete. The phases were separated and the aqueous phase washed with methylene chloride. The combined organic phases were dried over anhydrous sodium sulfate, filtered and evaporated. The residue was flash chromatographed on silica gel eluted with 10–20% ethyl acetate-hexane to give the epoxy compound which was converted by reaction with 1-methyl-5-carbomethoxy-2-thioimidazole to the desired product utilizing the general procedure of Example 1(a) and 1(b) (mp 112°–113° C.).

Analysis for $C_{22}H_{38}N_2O_4S$: Calculated: C, 61.42; H, 9.00; N, 6.51; S, 7.44. Found: C, 61.38; H, 8.72; N, 6.45; S, 7.70.

EXAMPLE 17

The intermediate 2-hydroxy-3-(1-methyl-5-carbomethoxy-2-imidazolylthio)-4(Z)-heptadecen-1-ol prepared as in Example 16(c) is oxidized with a saturated solution of periodic acid in diethyl ether to give 2-(1-methyl-5-carbomethoxy-2-imidazolylthio)-3(Z)-hexadecen-1-al. The latter compound is reduced in methanol solution with sodium borohydride and the resulting 2-(1-methyl-5-carbomethoxy-2-imidazolylthio)-3(Z)-hexadecen-1-ol is hydrolyzed with sodium hydroxide to yield 2-(1-methyl-5-carboxy-2-imidazolylthio)-3(Z)-hexadecen-1-ol.

EXAMPLE 18

The intermediate 2-(1-methyl-5-carbomethoxy-2-imidazolylthio)-3(Z)-hexadecen-1-al prepared as described in Example 17, in acetone solution, is oxidized under argon with Jones reagent to give 2-(1-methyl-5-carbomethoxy-2-imidazolylthio)-3(Z)-hexadecenoic acid. The latter compound is hydrolyzed with sodium hydroxide to provide 2-(1-methyl-5-carboxy-2-imidazolylthio)-3(Z)-hexadecenoic acid.

EXAMPLE 19

Preparation of 4-Hydroxy-5-(5-carboxymethyl-1,4-dimethyl-2-imidazolylthio)-6(Z)-nonadecenoic Acid A mixture of 5-carbethoxy-1,4-dimethyl-2-thioimidazole (21 g, 0.1 mole), 4-methoxybenzyl chloride (18 g, 0.11 mole) and tetrabutylammonium iodide (4.6 g, 0.01 mole) in toluene (1.5 L) was stirred with 40% aqueous sodium hydroxide (120 ml) for 16 hours at 25° C. The organic phase was washed with water, dried with sodium sulfate and concenetrated in vacuo to give 5-carbethoxy-1,4-dimethyl-2-(4-methoxybenzylthio)imidazole.

5-Carbethoxy-1,4-dimethyl-2-(4-methoxybenzylthio)imidazole (31 g, 0.1 mole) dissolved in ether (250 ml) was added dropwise to a solution of aluminum hydride in ether stirred at 0° C. [the aluminum hydride in ether was prepared by adding lithium aluminum hydride (7.4 g, 0.19 mole) in portions to a solution of aluminum chloride (8.6 g, 0.065 mole) stirred in ether (200 ml) at 0° C.]. The mixture was stirred at 0° C. for 1 hour, treated with water and 10% aqueous sodium hydroxide, filtered and concentrated in vacuo. The resulting oil was dissolved in methylene chloride, dried with magnesium sulfate, filtered and concentrated in vacuo to give 1,4-dimethyl-5-hydroxymethyl-2-(4-methoxybenzylthio)imidazole.

A mixture of 1,4-dimethyl-5-hydroxymethyl-2-(4-methoxybenzylthio)imidazole (1 g, 4 mmoles) and manganese dioxide (1.3 g, 15 mmoles) in methylene chloride (50 ml) was stirred at 25° C. for 16 hours. The mixture was filtered and the filtrate concentrated in vacuo to give 1,4-dimethyl-5-formyl-2-(4-methoxybenzylthio)imidazole.

1,4-Dimethyl-5-formyl-2-(4-methoxybenzylthio)imidazole (8 g, 0.03 mole) in tetrahydrofuran (30 ml) was added to a mixture prepared by adding sodium hydride (1.8 g, 38 mmoles) to a solution of methyl methylsulfinylmethylsulfide (4.7 g, 38 mmoles) in tetrahydrofuran. The mixture was stirred for 16 hours, concentrated in vacuo and the residue was partitioned between water and methylene chloride. The organic phase was dried with sodium sulfate, concentrated in vacuo and the residue chromatographed on silica gel eluted with ethyl acetate to give 1,4-dimethyl-2-(4-methoxybenzylthio)-5-[2-(methylsulfinyl)-2-(methylthio)ethenyl]imidazole.

1,4-Dimethyl-2-(4-methoxybenzylthio)-5-[2-methylsulfinyl)-2-(methylthio)ethenyl]imidazole (5.7 g, 15 mmoles) dissolved in ethanol (30 ml) was treated with hydrogen chloride at 0° C. for 20 minutes, stirred at 25° C. for 16 hours and concentrated in vacuo. The residue was partitioned between methylene chloride and 5% aqueous sodium carbonate. The organic phase was washed, dried with sodium sulfate and concentrated in vacuo to give 5-(carbethoxymethyl)-1,4-dimethyl-2-(4-methoxybenzylthio)imidazole: mp 158.5°–160° C.

5-(Carbethoxymethyl)-1,4-dimethyl-2-(4-methoxybenzylthio)imidazole (1 g, 3 mmoles) and mercuric acetate (3.3 g, 10 mmoles) in methanol (25 ml) were stirred for 16 hours, treated with excess hydrogen sulfide and filtered. The filtrate was concentrated in vacuo and the residue triturated with ether-hexane to give 5-(carbethoxymethyl)-1,4-dimethyl-2-thioimidazole.

Employing the general procedure of Example 1(a) and 1(b), methyl 4,5-epoxy-6(Z)-nonadecenoate (454 mg, 1.4 mmole) was reacted with 5-(carbethoxymethyl)-1,4-dimethyl-2-thioimidazole (454 mg, 2 mmoles) to afford the desired compound as a solid (mp 143°–144° C.).

Analysis for $C_{26}H_{44}N_2O_5S$: Calculated: C, 62.87; H, 8.92; N, 5.63. Found: C, 63.12; H, 8.82; N, 5.53.

EXAMPLE 20

Preparation of
4-Hydroxy-5-(5-carboxy-4-ethyl-1-methyl-2-imidazolylthio)-6-(Z)-nonadecenoic Acid Employing the general procedure of Example 1(c), ethyl 2-chloropropionylacetate afforded 5-carbethoxy-4-ethyl-1-methyl-2-thioimidazole (mp 158°–160° C.).

Employing the general procedure of Example 1(a) and 1(b), methyl 4,5-epoxy-6(Z)-nonadecenoate (636 mg, 2 mmoles) was reacted with 5-carbethoxy-4-ethyl-1-methyl-2-thioimidazole (720 mg, 3.4 mmoles) to afford the desired compound as a solid (mp 125.5°–126.5° C.).

Analysis for $C_{26}H_{44}N_2O_5S$: Calculated: C, 62.87; H, 8.93; N, 5.64, Found: C, 62.87; H, 8.78; N, 5.59.

EXAMPLE 21

Preparation of
4-Hydroxy-5-(5-carboxy-1-methyl-4-propyl-2-imidazolylthio)-6(Z)-nonadecenoic Acid Employing the general procedure of Example 1(c), ethyl 2-chlorobutyrylacetate afforded 5-carbethoxy-1-methyl-4-propyl-2-thioimidazole (mp 138°–141° C.).

Employing the general procedure of Example 1(a) and 1(b), methyl 4,5-epoxy-6(Z)-nonadecenoate (600 mg, 1.8 mmole) was reacted with 5-carbethoxy-1-methyl-1-propyl-2-thioimidazole (600 mg, 2.6 mmoles) to afford the desired compound as a solid (mp 117°–119° C.).

Analysis for $C_{27}H_{46}N_2O_5S$: Calculated: C, 63.49; H, 9.07; N, 5.48. Found: C, 63.45; H, 8.97; N, 5.43.

EXAMPLE 22

Preparation of
4-Hydroxy-5-(5-carboxy-4-isopropyl-1-methyl-2-imidazolylthio)-6(Z)-nonadecenoic Acid Employing the general procedure of Example 1(c), ethyl 2-chloro-4-methyl propionylacetate afforded 5-carbethoxy-4-isopropyl-1-methyl-2-thioimidazole.

Employing the general procedure of Example 1(a) and 1(b), methyl 4,5-epoxy-6(Z)-nonadecenoate (500 mg, 1.5 mmole) was reacted with 5-carbethoxy-4-isopropyl-1-methyl-2-thioimidazole to afford the desired compound as a solid (mp 47°–49° C.).

Analysis for $C_{27}H_{46}N_2O_5S$: Calculated: C, 63.49; H, 9.07; N, 5.48. Found: C, 63.25; H, 9.08; N, 5.50.

EXAMPLE 23

Preparation of
4-Hydroxy-5-[5-(2-carboxyethyl)-1,4-dimethyl-2-imidazolylthio]-6(Z)-nonadecenoic Acid A mixture of 1,4-dimethyl-5-formyl-2-(4-methoxybenzylthio)imidazole (1.7 g, 6 mmoles) and methyl (triphenylphosphoranylidene)acetate (4.8 g, 14 mmoles) in toluene (50 ml) was heated to reflux for 16 hours, cooled and concentrated in vacuo. The residue was triturated with ether, filtered and the filtrate was concentrated in vacuo. The residue was chromatographed on silica eluted with hexane-ethyl acetate (3:2) to give 5-[2-(carbethoxy)-ethenyl]-1,4-dimethyl-2-(4-methoxybenzylthio)imidazole (mp 165°–167° C.).

A mixture of 5-[2-(carbethoxy)ethenyl]-1,4-dimethyl-2-(4-methoxybenzylthio)imidazole (600 mg, 1.7 mmole) and potassium azodicarboxylate (29 g, 0.17 mole) in methanol (50 ml) was stirred and treated with acetic acid (7 g, 0.12 mole). The mixture was concentrated in vacuo, partitioned between methylene chloride and 5% aqueous sodium carbonate, and the organic phase was concentrated in vacuo. The residue was chromatographed on silica gel eluted with ethyl acetate to give 5-[2-(carbethoxy)ethyl]-1,4-dimethyl-2-(4-methoxybenzylthio)imidazole (mp 63° C.).

Following the general procedure of Example 19, 5-[2-(carbethoxy)ethyl]-1,4-dimethyl-2-(4-methoxybenzylthio)imidazole was reacted with mercuric acetate to afford 5-[2-(carbethoxy)ethyl]-1,4-dimethyl-2-thioimidazole.

Following the general procedure of Example 1(a) and 1(b), ethyl 4,5-epoxy-6(Z)-nonadecenoate (100 mg, 0.3 mmole) was reacted with 5-[2-(carbethoxy)ethyl]-1,4-dimethyl-2-thioimidazole (144 mg, 0.6 mmole) to afford the desired compound as a solid (mp 93°–94° C.).

Analysis for $C_{27}H_{46}N_2O_5S$: Calculated: C, 63.49; H, 9.07; N, 5.48. Found: C, 63.34; H, 8.94; N, 5.42.

EXAMPLE 24

Preparation of
4-Hydroxy-5-(5-Aminocarbonylmethyl-1,4-dimethyl-2-imidazolylthio)-6(Z)-nonadecenoic Acid A solution of 5-carbethoxymethyl-1,4-dimethyl-2-(4-methoxybenzylthio)imidazole (2 g, 6 mmoles) in methanol (15 ml) was cooled in an acetone/dry ice bath and treated with liquid ammonia (15 ml). The mixture was warmed to 25° C. and concentrated in vacuo to afford 5-(aminocarbonylmethyl)-1,4-dimethyl(-2-(4-methoxybenzylthio)imidazole.

Following the general procedure of Example 19, 5-(aminocarbonylmethyl)-1,4-dimethyl-2-(4-methoxybenzylthio)imidazole was reacted with mecuric acetate to afford 5-(aminocarbonylmethyl)-1,4-dimethyl-2-thioimidazole.

Following the general procedure of Example 1(a) and 1(b), ethyl 4,5-epoxy-6(Z)-nonadecenoate was reacted with 5-(aminocarbonylmethyl)-1,4-dimethyl-2-thioimidazole to afford the desired compound as an amorphous solid (structure confirmed by infra red spectral analysis).

EXAMPLE 25

Preparation of 4-Hydroxy-5-(5-carboxy-1,4-dimethyl-2-imidazolylthio)-18-methyl-6(Z),17-nonadecadienoic Acid a. 12-Methyl-11-tridecenyl-triphenylphosphonium Bromide 1-Bromo-11-hydroxyundecane (5 g, 20 mmoles) dissolved in methylene chloride (30 ml) was added to a suspension of pyridinium chlorochromate (6.4 g, 30 mmoles) in methylene chloride (25 ml) and stirred for 2 hours. The mixture was diluted with ether, filtered and concentrated in vacuo to afford 1-bromo-11-oxoundecane.

Isopropyltriphenylphosphonium iodide (6 g, 14 mmoles) was suspended in tetrahydrofuran (120 ml), stirred at −40° C. and treated with n-butyllithium (14 mmoles) dissolved in hexane (2.5M). The mixture was stirred at −40° C. for 15 minutes, cooled to −75° C. and treated with a solution of 1-bromo-11-oxoundecane (2.8 g, 11.5 mmoles) in tetrahydrofuran (30 ml). The mixture was stirred at −75° C. for 15 minutes, allowed to warm to 25° C. and concentrated in vacuo. The residue was triturated with hexane, filtered and the filtrate concentrated in vacuo. The residue was chromatographed on silica gel eluted with hexane to afford 1-bromo-12-methyl-11-tridecene.

1-Bromo-12-methyl-11-tridecene (4.4 g, 16 mmoles) and triphenylphosphine (4.65 g, 17 mmoles) dissolved in acetonitrile (80 ml) were heated to reflux for 4 days, cooled and concentrated in vacuo. The residue was chromatographed on silica gel eluted with chloroform and then with methanol-chloroform (2:3). Fractions containing the product were concentrated in vacuo, triturated with ether, filtered and dried in vacuo to afford the desired phosphonium salt.

b. Methyl 4,5-epoxy-18-methyl-6(Z),17-nonadecadienoate

12-Methyl-11-tridecenyl-triphenylphosphonium bromide (2 g, 3.7 mmoles) suspended in tetrahydrofuran (10 ml) was stirred at 0° C. and treated with n-butyllithium (3.7 mmoles) dissolved in hexane (2.7M). The mixture was cooled to −75° C. and treated with a solution of methyl 4,5-epoxy-6-oxohexanoate (0.5 g, 3.4 mmoles) in tetrahydrofuran (10 ml). The mixture was stirred at −75° C. for 45 minutes, allowed to warm to 25° C., poured into ice water containing 1% diethylamine, and extracted with ethyl acetate-ether. The organic phase was washed, dried with magnesium sulfate and concentrated in vacuo. The residue was chromatographed on silica eluted with ethyl acetate-hexane-diethylamine (5:95:0.1) to give the desired product.

c. 4Hydroxy-5-(5-carboxy-1,4-dimethyl-2-imidazoylthio)-18-methyl-6(Z),17-nonadecadienoic Acid Employing the general procedure of Example 1(a) and 1(b), methyl 4,5-epoxy-18-methyl-6(Z),17-nonadecadienoate was reacted with 5-carbethoxy-1,4-dimethyl-2-thioimidazole to afford the desired product as a solid (mp 135°-138° C.); −log $K_B$ value 7.5.

Analysis for $C_{26}H_{42}N_2O_5S$: Calculated: C, 63.13; H, 8.56; N, 5.66. Found: C,63.04; H, 8.48; N, 5.49.

EXAMPLE 26

Preparation of 4-Hydroxy-5-(5-carboxy-1,4-dimethyl-2-imidazolylthio)-15-phenyl-6(Z)-pentadecenoic Acid a. 9-Phenyloctyl-triphenylphosphonium Bromide A solution of 9-phenyloctanol (7 g, 32 mmoles) in methylene chloride (150 ml) stirred at 0° C. was treated with carbon tetrabromide (13.7 g, 41 mmoles) and triphenylphosphine (10.4 g, 40 mmoles). The mixture was stirred at 25° C. for 45 minutes and concentrated in vacuo. The residue was triturated with hexane and the hexane phase was concentrated in vacuo and chromatographed on silica eluted with hexane to afford 9-phenyloctyl bromide.

9-Phenyloctyl bromide (9.1 g, 32.5 mmoles) and triphenylphosphine (9.3 g, 35.5 mmoles) were dissolved in acetonitrile (100 ml) and heated to reflux for 4 days. The mixture was concentrated in vacuo, washed with ether and chromatographed on silica eluted with methanol-methylene chloride (1:9). Fractions containing the desired phosphonium salt were concentrated in vacuo, dissolved in methylene chloride, dried with magnesium sulfate, filtered and concentrated in vacuo to give 9-phenyloctyl-triphenylphosphonium bromide.

b. Methyl 4,5-epoxy-15-phenyl-6(Z)-pentadecenoate

Employing the general procedure of Example 25(b), 9-phenyloctyl-triphenylphosphonium bromide (2 g, 3.6 mmoles) was converted to the ylid and reacted with methyl 4,5-epoxy-6-oxohexanoate (0.5 g, 3.3 mmoles) to afford the desired product.

c. 4-Hydroxy-5-(5-carboxy-1,4-dimethyl-2-imidazolylthio)-15-phenyl-6(Z)-pentadecenoic Acid Employing the general procedure of Example 1(a) and 1(b), methyl 4,5-epoxy-15-phenyl-6(Z)-pentadecenoate was reacted with 5-carbethoxy-1,4-dimethyl-2-thioimidazole to afford the desired product as a solid (mp 118°-119.5° C.); −log $K_B$ value 6.6.

Analysis for $C_{27}H_{38}N_2O_5S.\frac{1}{4}H_2O$: Calculated: C, 63.94; H, 7.65; N, 5.52. Found: C, 63.92; H, 7.49; N, 5.88.

EXAMPLE 27

As a specific embodiment of a composition of this invention, an active ingredient, such as the compound of Example 1(b), is dissolved in 25 mM sodium carbonate at a concentration of 0.4 percent and aerosolized from a nebulizer operating at an air flow adjusted to deliver the desired aerosolized weight of drug.

EXAMPLE 28

As an additional specific embodiment of a composition of this invention, an active ingredient, such as the compound of Example 3, is admixed with mannitol at a concentration of 1.0 percent and administered from a powder inhalation device adjusted to deliver the desired weight of drug.

What is claimed is:

1. A compound represented by the following structural formula (I):

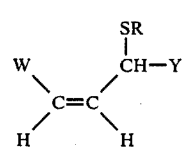

(I)

wherein m is 9, 10, 11, 12 or 13; W is $CH_3(CH_2)_m$—, 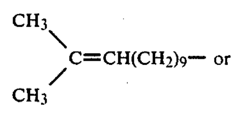 or phenyl$(CH_2)_8$—;

Y is selected from the group consisting of —CO$_2$H —CH$_2$OH,

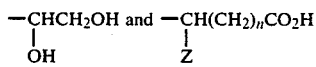

wherein n is 2 or 3 and Z is hydroxyl or hydrogen; and R is selected from the imidazolyl radical of the following formulae (A) or (B)

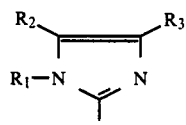

wherein R$_1$ is hydrogen, C$_1$ to C$_4$ alkyl or C$_3$ to C$_4$ alkenyl, R$_2$ is hydrogen, C$_1$ to C$_4$ alkyl, carboxyl or carboxamido, or either —(CH$_2$)$_p$CO$_2$H or —(CH$_2$)$_p$CONH$_2$, wherein p is 1 or 2, when R$_1$ and R$_3$ are hydrogen or C$_1$ to C$_4$ alkyl, and R$_3$ is hydrogen, C$_1$ to C$_4$ alkyl or —CH$_2$CO$_2$H with the proviso that R$_1$, R$_2$ and R$_3$ cannot all be hydrogen; provided that when Y is

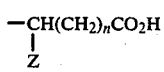

wherein Z is OH and n is 2 or 3,
(a) R$_2$ is not carboxamido;
(b) only one of R$_1$, R$_2$, and R$_3$ is hydrogen;
(c) R$_3$ must be —CH$_2$CO$_2$H if R$_2$ is hydrogen or C$_1$ to C$_4$ alkyl; and
(d) R$_2$ must be COOH, —(CH$_2$)$_p$COOH or —(CH$_2$)$_p$CONH$_2$ wherein p is 1 or 2 if R$_3$ is hydrogen or alkyl; or

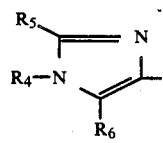

wherein R$_4$ is hydrogen, C$_1$ to C$_4$ alkyl or C$_3$ to C$_4$ alkenyl, R$_5$ is hydrogen, C$_1$ to C$_4$ alkyl or C$_3$ to C$_4$ alkenyl and R$_6$ is hydrogen or carboxyl with the proviso that R$_4$, R$_5$ and R$_6$ cannot all be hydrogen; provided that when Y is

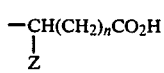

wherein Z is OH and n is 2 or 3, R$_6$ is not hydrogen and R$_4$ and R$_5$ cannot both be hydrogen; or a pharmaceutically acceptable salt thereof.

2. A compound of claim 1, formula (I) wherein Y is

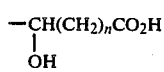

which is represented by the following formula (II)

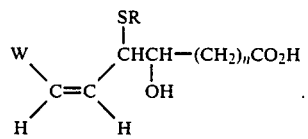

3. A compound of claim 2 wherein W is CH$_3$(CH$_2$)$_m$— and R is the imidazolyl radical of the formula (A).

4. A compound of claim 3 wherein m is 11 and n is 2 which is represented by the following formula (III)

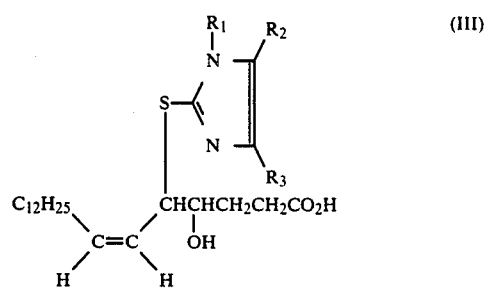

5. A compound of claim 4 wherein R$_1$ is an alkyl radical containing from one to four carbon atoms or an alkenyl radical containing from three to four carbon atoms.

6. A compound of claim 5 wherein R$_1$ is an alkyl radical.

7. A compound of claim 4 which is 4-hydroxy-5-[4(5)-carboxy-2-imidazolylthio]-6(Z)-nonadecenoic acid.

8. A compound of claim 3 wherein m is 11 and n is 3 which is represented by the following structural formula (IV)

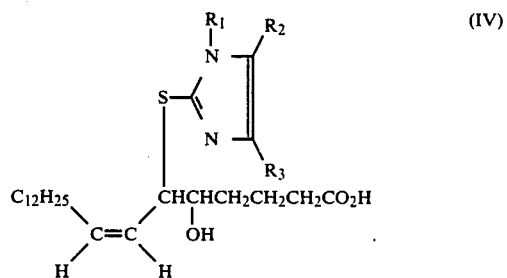

9. A compound of claim 8 wherein R$_1$ is an alkyl radical containing from one to four carbon atoms.

10. A compound of claim 2 wherein W is CH$_3$(CH$_2$)$_m$— and R is the imidazolyl radical of the formula (B).

11. A compound of claim 10 wherein m is 11 and n is 2 which is represented by the following structural formula (V)

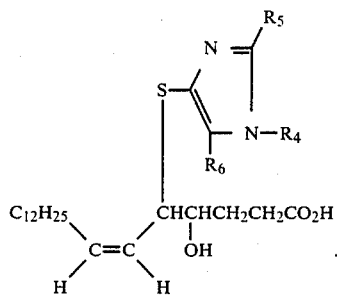

12. A compound of claim 11 wherein $R_4$ is an alkyl radical containing from one to four carbon atoms.

13. A compound of claim 12 which is 4-hydroxy-5-(1-methyl-5-carboxy-4-imidazolylthio)-6(Z)-nonadecenoic acid.

14. A compound which is represented by the following formula (VI)

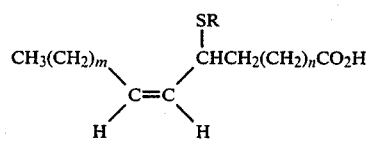

wherein m is 9, 10, 11, 12, or 13; n is 2 or 3; and R is selected from the imidazolyl radical of the following formulae (A) or (B)

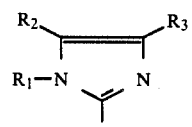

wherein $R_1$ is hydrogen, $C_1$ to $C_4$ alkyl or $C_3$ to $C_4$ alkenyl, $R_2$ is hydrogen, $C_1$ to $C_4$ alkyl, carboxyl or carboxamido, or either —$(CH_2)_pCO_2H$ or —$(CH_2)_pCONH_2$, wherein p is 1 or 2, when $R_1$ and $R_3$ are hydrogen or $C_1$ to $C_4$ alkyl, and $R_3$ is hydrogen, $C_1$ to $C_4$ alkyl or —$CH_2CO_2H$ with the proviso that $R_1$, $R_2$ and $R_3$ cannot all be hydrogen or

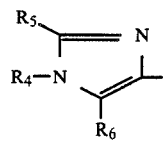

wherein $R_4$ is hydrogen, $C_1$ to $C_4$ alkyl or $C_3$ to $C_4$ alkenyl, $R_5$ is hydrogen, $C_1$ to $C_4$ alkyl or $C_3$ to $C_4$ alkenyl and $R_6$ is hydrogen or carboxyl with the proviso that $R_4$, $R_5$ and $R_6$ cannot all be hydrogen; or a pharmaceutically acceptable salt thereof.

15. A compound of claim 14 wherein m is 11, n is 2 and R is the imidazolyl radical of the formula (A).

16. A compound of claim 15 which is 5-(1-methyl-5-carboxy-2-imidazolylthio)-6(Z)-nonadecenoic acid.

17. A compound which is represented by the following structure (VIII)

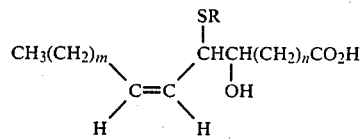

wherein m is 9, 10, 11, 12, or 13 and R is selected from the imidazolyl radical of the following formula (A) or (B)

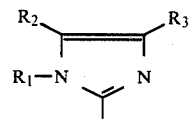

wherein $R_1$ is hydrogen, $C_1$ to $C_4$ alkyl or $C_3$ to $C_4$ alkenyl, $R_2$ is hydrogen, $C_1$ to $C_4$ alkyl, carboxyl or carboxamido, or either —$(CH_2)_pCO_2H$ or —$(CH_2)_pCONH_2$, wherein p is 1 or 2, when $R_1$ and $R_3$ are hydrogen or $C_1$ to $C_4$ alkyl, and $R_3$ is hydrogen, $C_1$ to $C_4$ alkyl or —$CH_2CO_2H$ with the proviso that $R_1$, $R_2$ and $R_3$ cannot all be hydrogen or

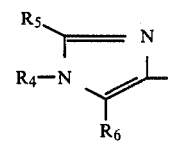

wherein $R_4$ is hydrogen, $C_1$ to $C_4$ alkyl or $C_3$ to $C_4$ alkenyl, $R_5$ is hydrogen, $C_1$ to $C_4$ alkyl or $C_3$ to $C_4$ alkenyl and $R_6$ is hydrogen or carboxyl with the proviso that $R_4$, $R_5$ and $R_6$ cannot all be hydrogen; or a pharmaceutically acceptable salt thereof.

18. A compound of claim 17 wherein m is 11 and R is the imidazolyl radical of the formula (A).

19. A compound of claim 18 which is 2-hydroxy-3-(1-methyl-5-carboxy-2-imidazolylthio)-4(Z)-heptadecen-1-ol.

20. A compound of claim 1, formula (I) wherein W is $CH_3(CH_2)_m$— and Y is —$CO_2H$ which is represented by the following structure (IX)

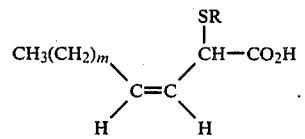

21. A compound of claim 20 wherein m is 11 and R is the imidazolyl radical of the formula (A).

22. A compound of claim 21 which is 2-(1-methyl-5-carboxy-2-imidazolylthio)-3(Z)-hexadecenoic acid.

23. A compound of claim 1, formula (I) wherein W is $CH_3(CH_2)_m$—,

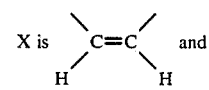

Y is —$CH_2OH$ which is represented by the following structure (X)

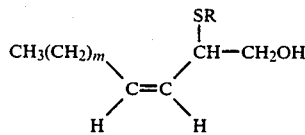

24. A compound of claim 23 wherein m is 11 and R is the imidazolyl radical of the formula (A).

25. A compound of claim 24 which is 2-(1-methyl-5-carboxy-2-imidazolythio)-3(Z)-hexadecen-1-ol.

26. A compond of claim 2 wherein W is

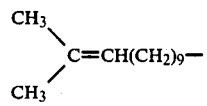

and R is the imidazolyl radical of the formula (A).

27. A compound of claim 26 which is 4-hydroxy-5-(5-carboxy-1,4-dimethyl-2-imidazolylthio)-18-methyl-6(Z), 17-nonadecadienoic acid.

28. A compound of claim 2 wherein W is phenyl $(CH_2)_8$— and R is the imidazolyl radical of the formula (A).

29. A compound of claim 28 which is 4-hydroxy-5-(5-carboxy-1,4-dimethyl-2-imidazolylthio)-15-phenyl-6(Z)-pentadecenoic acid.

30. A compound of claim 6 which is 4hydroxy-5-(1-methyl-4-carboxymethyl-2-imidazolylthio)-6(Z)-nonadecenoic acid; 4-hydroxy-5-(1-methyl-5-carboxy-2-imidazolylthio)-6(Z)-nonadecenoic acid; 4-hydroxy-5-(1,4-dimethyl-5-carboxy-2-imidazolylthio)-6(Z)-nonadecenoic acid; 4-hydroxy-5-(5-carboxymethyl-1,4-dimethyl-2-imidazolylthio)-6-(Z)-nonadecenoic acid; 4-hydroxy-5-(5-carboxy-4-ethyl-1-methyl-2-imidazolylthio)-6(Z)-nonadecenoic acid; 4-hydroxy-5-(5-carboxy-1-methyl-4-propyl-2-imidazolylthio)-6(Z)-nonadecenoic acid; 4-hydroxy-5-(5-carboxy-4isopropyl-1-methyl-2-imidazolylthio)-6(Z)-nonadecenoic acid; or 4-hydroxy-5-[5-(2-carboxyethyl)-1,4-dimethyl-2-imidazolylthio]-6(Z)-nonadecenoic acid.

31. A pharmaceutical composition for antagonizing the effects of leukotrienes comprising a pharmaceutical carrier or diluent and an amount sufficient to antagonize said effects of a compound of claim 1, formulae (I) or (IA), or a pharmaceutically acceptable salt thereof.

32. A pharmaceutical composition according to claim 31 in the form of an aerosol formulation or a sterile solution, or in a form suitable for administration by inhalation, parenteral administration or topical administration.

* * * * *